United States Patent [19]

Mulhollan et al.

[11] Patent Number: 4,597,390
[45] Date of Patent: Jul. 1, 1986

[54] SURGICAL NEEDLE MANIPULATOR

[76] Inventors: James S. Mulhollan, 3401 Foxcroft Rd., Little Rock, Ark. 72207; Lionel Starr, 8806 Patricia Lynn, Sherwood, Ark. 72116

[21] Appl. No.: 595,818

[22] Filed: Apr. 2, 1984

[51] Int. Cl.⁴ .............................................. A61B 17/06
[52] U.S. Cl. .................................... 128/340; 112/169
[58] Field of Search ................ 128/340, 339; 223/102, 223/104; 112/226, 169

[56] References Cited

U.S. PATENT DOCUMENTS

| | | | |
|---|---|---|---|
| 1,648,451 | 11/1927 | Fisher | 223/102 |
| 3,344,790 | 10/1967 | Dorner | 223/104 |
| 3,878,848 | 4/1975 | Hiebert | 128/340 |
| 4,165,745 | 8/1979 | Heifetz | 128/340 |
| 4,345,601 | 8/1982 | Fukuda | 128/339 |
| 4,493,323 | 1/1985 | Albright et al. | 128/340 |

Primary Examiner—Robert Peshock
Assistant Examiner—John G. Weiss
Attorney, Agent, or Firm—Hill, Van Santen, Steadman & Simpson

[57] ABSTRACT

A device for manipulating a surgical needle which has been set in tissue is provided which comprises a tube with a telescoping rod therein, the tube and rod having a diametrical slot in one end forming a bifurcated slot. The tube and rod are relatively rotatable resulting in the slot portions being movable in and out of alignment. When the slot portions are in alignment the shank of the needle can be received in the slots, and as they are moved out of alignment, the needle is grasped by the side walls of the slots. Diametrical holes in the tube and rod are also provided forming a bifurcated passage for gripping the tip of the needle in a similar manner.

11 Claims, 6 Drawing Figures

U.S. Patent    Jul. 1, 1986    4,597,390
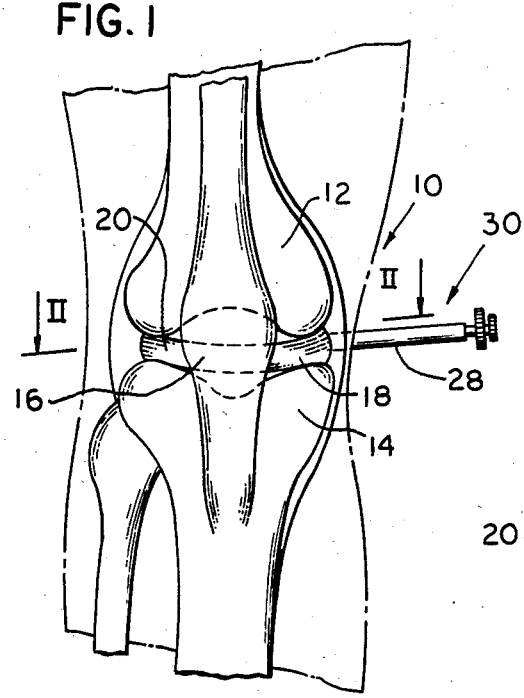
FIG. 1
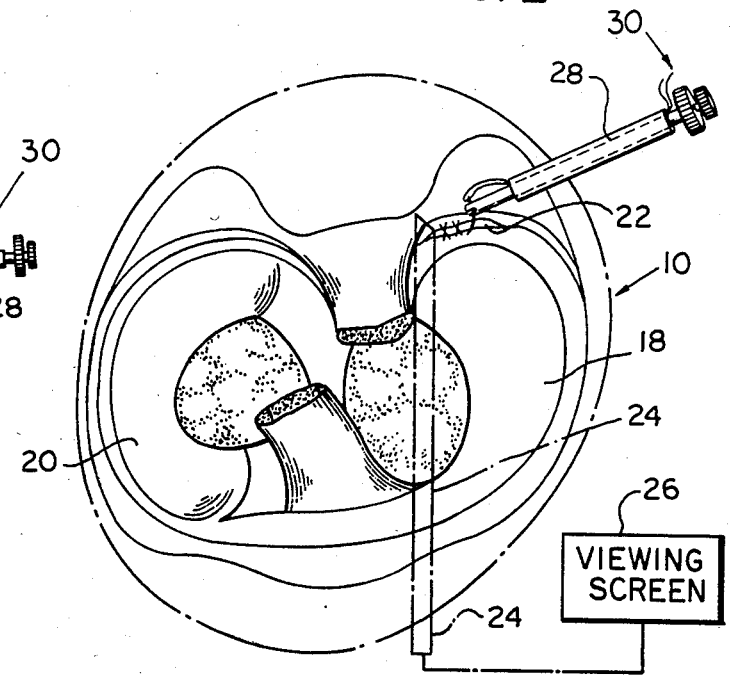
FIG. 2
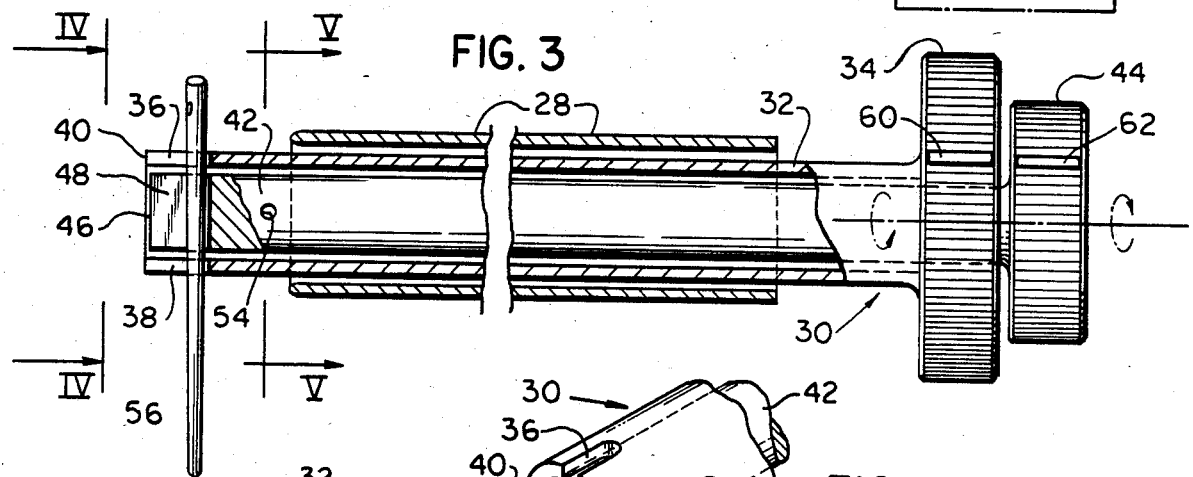
FIG. 3
FIG. 6
FIG. 4
FIG. 5

SURGICAL NEEDLE MANIPULATOR

BACKGROUND OF THE INVENTION

1. Field of the Invention

The present invention relates to surgical instruments and more particularly to a surgical needle manipulator for use in manipulating a needle in a limited access area.

2. DESCRIPTION OF THE PRIOR ART

Manipulation of surgical needles is generally done with the assistance of a mechanical gripping device referred to as a needle holder or thumb forceps because of the relatively small size of the needle. Such gripping devices commonly used employ a pair of opposed gripping surfaces on a scissors-like device which also can include a ratchet-type lock to lock the gripping surfaces against the needle. Because of the pivoting scissorslike construction, the device requires some lateral room for opening and closing upon the needle. While this type of instrument is useful in many surgical procedures, the shear size of the instrument prevents its use in surgical procedures where the stitch being set by the needle is in an area of limited accessibility, for instance in the interior of the human body to which access is provided percutaneously through a cannula. Generally, such cannulas may have interior diameters of 5 to 10 millimeters which prevents the usage of standard surgical instruments.

SUMMARY OF THE INVENTION

The present invention provides a surgical needle manipulator instrument which can be used to manipulate a surgical needle at a remote and relatively inaccessible location, including a location accessed only through a relatively small cannula. The device comprises a tube and an interior shaft which can be axially rotated relative to one another from an accessible location. Both the tube and the shaft have a slot formed diametrically across their distant ends and have a hole formed through a sidewall near the distant ends which can be aligned by rotation between the two elements.

The slot is sized to receive the shank of the needle and a slight rotation between the tube and the shaft will provide a secure grip on the needle shank. This allows the needle to be rotated to set a stitch. Once the needle has been rotated into the tissue, only the eye and the tip are exposed. The holes in the tube and shaft are then aligned and placed over the exposed needle tip, and the two elements are rotated slightly relative to each other to grip the end of the needle. This allows the needle to be pulled through the tissue where it will be accessible for another instrument to withdraw the needle from the operating zone.

BRIEF DESCRIPTION OF THE DRAWINGS

FIG. 1 is a front elevational view of a human knee and showing a needle manipulator embodying the principles of the present invention;

FIG. 2 is a top sectional view throuqh the knee showing the needle manipulator and an arthroscopic viewing means;

FIG. 3 is a partial side sectional and elevational view of the needle manipulator embodying the principles of the present invention;

FIG. 4 is an end view of the needle manipulator ripping a needle taken generally along the lines IV—IV of FIG. 3;

FIG. 5 is an end elevational view of the needle manipulator grasping the tip of the needle and taken generally along the lines V—V; and FIG. 6 is a partial perspective view of the end of the needle manipulator showing the slot and hole alignments.

DESCRIPTION OF THE PREFERRED EMBODIMENTS

Although the principles of the present invention are applicable to any device suitable in surgical procedures whether performed on humans or animals, a particular utility is effected in human knee surgery where the problems of surgery are particularly acute. Accordingly, as an illustrative exemplification of our invention in FIG. 1 there is shown a human knee joint generally at 10 which provides an environment in which the present invention is especially useful. Within the knee joint 10 there is shown the femur bone 12, the tibia bone 14, the patella or knee cap 16 and the medial meniscus 18 and lateral meniscus 20. The menisci 18, 20 are cartilage structures in contact with both the femur 12 and tibia 14. As seen in FIG. 2, the menisci are crescent shaped with a central open area. Certain injuries to the knee cause tears to the menisci such as that shown at 22 in FIG. 2.

Arthroscopes are available which have a light and optics probe, as shown at 24, which can be inserted through a puncture wound for viewing the interior portion of the knee joint 10 through a viewing lens or screen shown schematically at 26. The arthroscope permits the physician or surgeon to see the tear 22 without surgically opening the knee to expose that portion of the joint.

A hollow cannula or tube 28 can be inserted through the skin around the knee joint to a position proximate to the tear 22 in the meniscus 18. Various instruments can be inserted through this cannula 28 to perform various surgical tasks. The present invention provides for an instrument which can be inserted through this cannula 28 to manipulate a surgical needle for setting a stitch in meniscus so that the tear 22 can be sewn shut to assist in the healing process without opening the knee to expose this portion of the knee joint. Such a procedure is greatly advantageous over previous methods of knee surgery in that healing time is drastically reduced to days instead of weeks. Rehabilitation of the knee joint after surgery is not required anywhere near the degree it has heretofore been required.

A surgical needle manipulator 30 is shown in each of the figures and is comprised of a tube 32 having a knurled flange 34 at one end and a pair of diametrically opposed slots 36, 38 formed at an end 40 opposite the knurled flange 34. The tube 32 has an outer diameter sufficiently lesser than the inner diameter of the cannula bore to afford a clearance to allow it to move loosely in the cannula 28. A typical tube diameter would be about 5 mm.

A rod or shaft 42 extends through the flange 34 and telescopically through the interior of the tube 32. An enlarged knurled end 44 is provided on the rod 42 which is positioned adjacent to the flange 34 of the tube 32. The rod 42 has a second end 46 which is flush with end 40 of the tube. The end 46 has a groove or slot 48 extending across the diameter of the rod 42 which is substantially identical to the slots 36, 38 in width and depth. The rod 42 can be rotated relative to the tube 32 such that the slot 48 in the rod 42 can be aligned with the slots 36, 38 in the tube. The aligned slots 36, 38 in the tube and the slot 48 in the rod form a bifurcated slot comprising two relatively rotatable slot portions which can be rotated in and out of alignment by relative rotation of the tube and the rod.

Holes 50, 52 are provided in a sidewall of the tube, diametrically opposed and a hole 54 is provided extending diametrically all the way through the rod 42 which can be aligned with the two holes 50, 52 in the tube. The aligned holes 50, 52 in the tube and the hole 54 in the rod form a bifurcated passage comprising two relatively rotatable passage portions which can be rotated in and out of alignment by relative rotation of the tube and the rod.

Use of the device is shown in FIGS. 4 and 5 wherein it is seen that a surgical needle 56 is partially inserted into tissue 58 adjacent the tear 22. The placement of the needle into the tissue would be done by another appropriate instrument. The needle manipulator 30 is passed through the cannula 28 into the area adjacent the tear 22 and is viewed by means of the arthroscope 24 which provides an end view of the device similar to the view seen in FIGS. 4 and 5. The knurled flange 34 and knurled end 44 of the tube 32 and shaft 42 are aligned rotationally by use of appropriate markings 60, 62 on those two ends. This rotation aligns the slot 48 in the rod 42 with the slots 36, 38 in the tube 32.

The slots have a width slightly greater than the width of the surgical needle 56 which has a curved shank 63. The needle manipulator 30 is pushed toward the needle 56 with the slots 36, 38 and 48 aligned with the shank 63 of the needle such that the needle is captured within the slots. The rod 42 is rotated relative to the tube 32 so that the needle 56 is gripped at a plurality of points by the slots. With the needle so grasped, it can be rotated through the tissue and across the tear 22 until the tip 64 is exposed above the tissue layer. The rod is again rotated relative to the tube 32 to align the slots, thereby releasing the gripping action on the needle shank to allow the needle manipulator 30 to be moved away from the needle.

With the slots aligned, the holes 50, 52 and 54 are also in alignment and they can be used to capture the tip 64 of the needle 56 as is seen in FIG. 5. Once the needle tip is captured in the hole 50 in the tube and the hole 54 in the rod 42, the rod is rotated slightly relative to the tube thus providing a gripping action on the needle tip. The gripping by the manipulator 30 allows for continued rotation of the needle 56 through the tissue until the needle 56 is completely withdrawn from the tissue 58 resulting in only the suture material 66 remaining in the tissue. The needle manipulator 30 is then removed from the cannula and another device is inserted to grasp and withdraw the needle allowing knots to be tied and passed down to the tear area.

Thus, there is provided a system for pulling a surgical needle through tissue into which it has been set in a location of limited accessibility which comprises a cannula positioned with a first end adjacent the area of limited accessibility and a second end exposed to an area of greater accessibility, a needle manipulator insertable through the cannula from the exposed end and having means for securely grasping the shank of the set needle. The manipulator includes means for directing the needle through the tissue until the tip of the needle is exposed and means for releasing the shank of the needle. The manipulator also includes means for grasping the tip of the needle to pull the needle entirely through the tissue and means for releasing the needle tip.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A device for manipulating a surgical needle, comprising: a hollow tube having knurled flange at one end and a pair of diametrically opposed slots at an opposite end, a rod member sized to telescopically fit within said hollow tube having a knurled flange at one end and a flat face with a diametrical slot formed therein at an opposite end, said rod member rotatable within said tube to permit alignment and misalignment between said slots in said tube and said slot in said rod member, whereby, said slots, upon alignment, can receive the shank of said surgical needle, and upon relative rotation of said rod member, said device will grip said needle for manipulation.

2. The device of claim 1 including a pair of diametrically opposed holes through said tube and a diametrical hole through said rod member which can be aligned with said holes in said tube, whereby, said holes, upon alignment, can receive the tip of said surgical needle, and upon relative rotation of said rod member, said device will grip said needle for manipulation.

3. The device of claim 1 wherein said knurled flanges have alignment markings thereon to assist in the alignment of said slots when viewing said knurled ends.

4. The device of claim 2 wherein said knurled flanges have alignment markings thereon to assist in the alignment of said holes when viewing said knurled ends.

5. A surgical needle manipulator comprising:

a bifurcated slot having two slot portions relatively rotatable for grasping the shank of a surgical needle which has been set into tissue, means for directing said needle through said tissue until the tip of said needle is exposed, means for releasing said shank of said needle, means for grasping said tip of said needle to pull said needle entirely through said tissue, means for releasing said needle tip.

6. A surgical needle manipulator according to claim 5 wherein said means for grasping said needle tip comprises a bifurcated passage having two passage portions relatively rotatable.

7. A surgical needle manipulator comprising:

means for grasping the shank of a surgical needle which has been set into tissue, which further comprises a bifurcated slot having two slot portions relatively rotatable, side walls of said slot portions forming gripping areas upon relative rotation of said portions, means for directing said needle through said tissue until the tip of said needle is exposed, means for releasing said shank of said needle, means for grasping said tip of said needle to pull said needle entirely through said tissue, means for releasing said needle tip.

8. A surgical needle manipulator comprising:

means for grasping the shank of a surgical needle which has been set into tissue, means for directing said needle through said tissue until the tip of said needle is exposed, means for releasing said shank of said needle, means for grasping said tip of said needle to pull said needle entirely through said tissue, which further comprises two members, each with a hole therethrough forming a bifurcated passage having two passage portions relatively rotatable in and out of alignment, side walls of said passage portions forming gripping areas upon relative rotation of said portions, means for releasing said needle tip.

9. A system for pulling a surgical needle through tissue into which it has been set in a location of limited accessibility comprising:

a cannula positioned with a first end adjacent said location of limited accessibility and with a second end exposed to an area of accessibility, a needle manipulator insertable through said second end of said cannula and having means for securely grasping the shank of said set needle, means for directing said needle through said tissue until the tip of said needle is exposed, means for releasing said shank of said needle, means for grasping said tip of said needle to pull said needle entirely through said tissue, and means for releasing said needle tip.

10. The device of claim 9 wherein said means for grasping the shank of said needle comprises a bifurcated slot having two slot portions relatively rotatable, side walls of said slot portions forming gripping areas upon relative rotation of said portions.

11. The device of claim 9 wherein said means for grasping said tip of said needle comprises two members, each with a hole therethrough forming a bifurcated passage having two passage portions relatively rotatable in and out of alignment, side walls of said passage portions forming gripping areas upon relative rotation of said portions.

* * * * *